US00PP27895P3

(12) United States Plant Patent
Hartmann

(10) Patent No.: US PP27,895 P3
(45) Date of Patent: Apr. 18, 2017

(54) BLUEBERRY PLANT NAMED 'A132-926'

(50) Latin Name: *Vaccinium*
Varietal Denomination: A132-926

(71) Applicant: Daniel Patrick Hartmann, South Haven, MI (US)

(72) Inventor: Daniel Patrick Hartmann, South Haven, MI (US)

( * ) Notice: Subject to any disclaimer, the term of this patent is extended or adjusted under 35 U.S.C. 154(b) by 165 days.

(21) Appl. No.: 14/121,868

(22) Filed: Oct. 28, 2014

(65) Prior Publication Data

US 2016/0120082 P1 Apr. 28, 2016

(51) Int. Cl.
*A01H 5/08* (2006.01)

(52) U.S. Cl.
USPC ..... Plt./157

(58) Field of Classification Search
USPC ..... Plt./157
See application file for complete search history.

*Primary Examiner* — Keith Robinson
(74) *Attorney, Agent, or Firm* — Flynn, Thiel, Boutell & Tanis, P.C.

(57) ABSTRACT

A new and distinct low-chilling blueberry (*Vaccinium*) variety 'A132-926'. The parents of 'A132-026' are 'Sharpblue' and 'Misty', inter-specific hybrids of several species. 'A132-926'

(a) is free flowering without the use of growth regulating chemicals,
(b) has very low chilling requirement,
(c) has fine berry quality,
(d) is adaptable for mechanical harvest,
(e) has early ripening of fruits,
(f) is resistant to *phytophthera cinammomii,*
(g) is resistant to foliar disease,
(h) has uniform ripening, and
(i) performs well in greenhouses.

7 Drawing Sheets

*Vaccinium* (interspecific crosses of *V. australe, V. darrowi, V. ashei* and *V. corymbosum*).

Variety denomination: 'A132-926'.

BACKGROUND OF THE INVENTION

The present invention relates to a blueberry variety 'A132-926' blueberry plant.

The closest known varieties are its male parent 'Sharpblue' (unpatented) and its female parent 'Misty' (unpatented) both interspecific hybrids.

The variety 'A132-026' was bred by the inventor, observed and tested in Grand Junction, Mich. 49056.

*Vaccinium* hybrid 'A132-926' was derived from a controlled hybrid cross with commercial varieties 'Sharpblue' (male) and 'Misty' (female). Plants were hybridized in Grand Junction, Mich. in 2005 and testing resumed of the variety from that date until the present.

SUMMARY OF THE VARIETY

The following is a summary of the description of the new and distinct variety of blueberry 'A132-026', its flower, fruit, stems, and foliage based on observations of specimen grown in Grand Junction, Mich.

'A132-926' is free flowering without the use of growth regulating chemicals. 'A132-926' is a multi-stemmed, erect shrub. Branches are spreading outward 3.5 feet (1.06 meter). It has a low chilling requirement compared to most commercial varieties. It's chilling requirements, 150 hours minimum to 600 hours maximum. Stems are cold tolerant to −10 F. It has the earliest fruiting of most commercial cultivars. The large fruits ripen uniformily.

Fruit quality is firm and with a small picking scar. The fruits are suitable for fresh markets, and can be stored for 21 days at temperatures 33 to 40 degrees F. (0.5 to 4.4 C) compared to Misty that if stored at the same temperatures can be stored for 12 days. First fruits begin ripening 10 days earlier than the leading low chill commercial cultivar 'Star'.

Pollinated and non-pollinated fruits of 'A132-926' are approximately the same size. Normally fruits of blueberry cultivars without seeds in the fruit (non-pollinated) are up 50% to 70% smaller than pollinated fruits, depending on the cultivar. This characteristic makes 'A132-926' particularly attractive to greenhouse growers because bee pollination is not required. 'A132-926' cultivar also grows in a wide variety of tropical to subtropical climates.

ASEXUAL REPRODUCTION OF THE VARIETY

'A132-926' was asexually propagated in a cultivated area in Grand Junction, Mich. in 2012 utilizing softwood cuttings. The plants so propagated have shown that the unique features of this new *Vaccinium* plant are stable and reproduce true to type in successive generations of asexual propagation. 'A132-926' can also be produced by in vitro methods.

BRIEF DESCRIPTION OF THE DRAWINGS

The accompanying photographs illustrate the overall appearance of the new and distinct variety of 'A132-926'. The age of the plants described in the BRIEF DESCRIPTION OF THE DRAWINGS is six (6) years.

Figure 1:
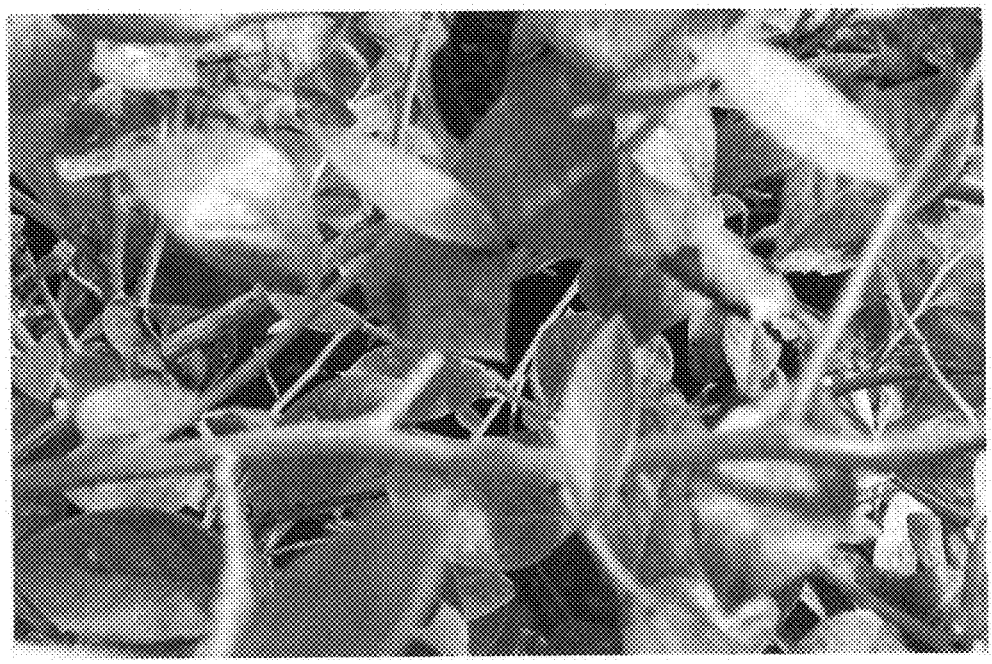
FIG. 1 Is a photograph illustration of the two year stems and leaves of 'A132-926' including their shape and approximate color.
Figure 2:
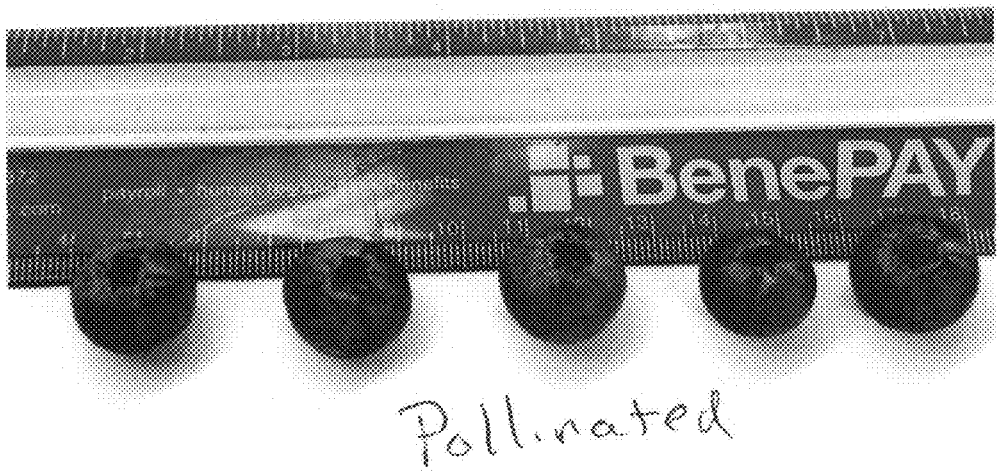
FIG. 2 Is a photographic illustration of the whole fruit of 'A132-926' with seeds (pollinated) including the shape and color of the berries.
Figure 3:
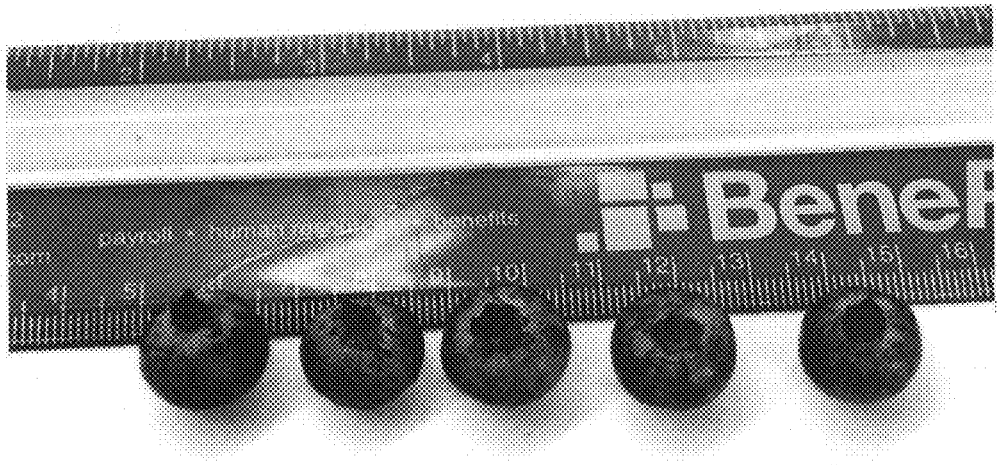
FIG. 3 Is a photographic illustration of the whole fruit of 'A132-926' without seeds (not pollinated).
Figure 4:
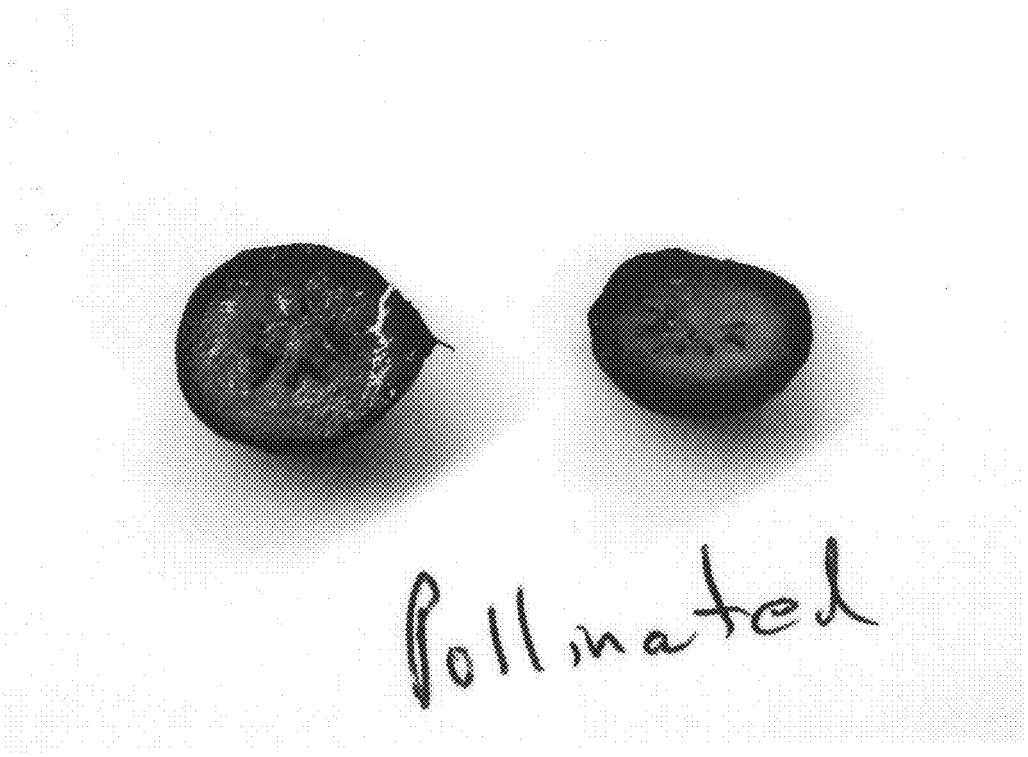
FIG. 4 Is a photographic illustration of slices of fruit with seeds (pollinated) from the plant 'A132-926'.
Figure 5:
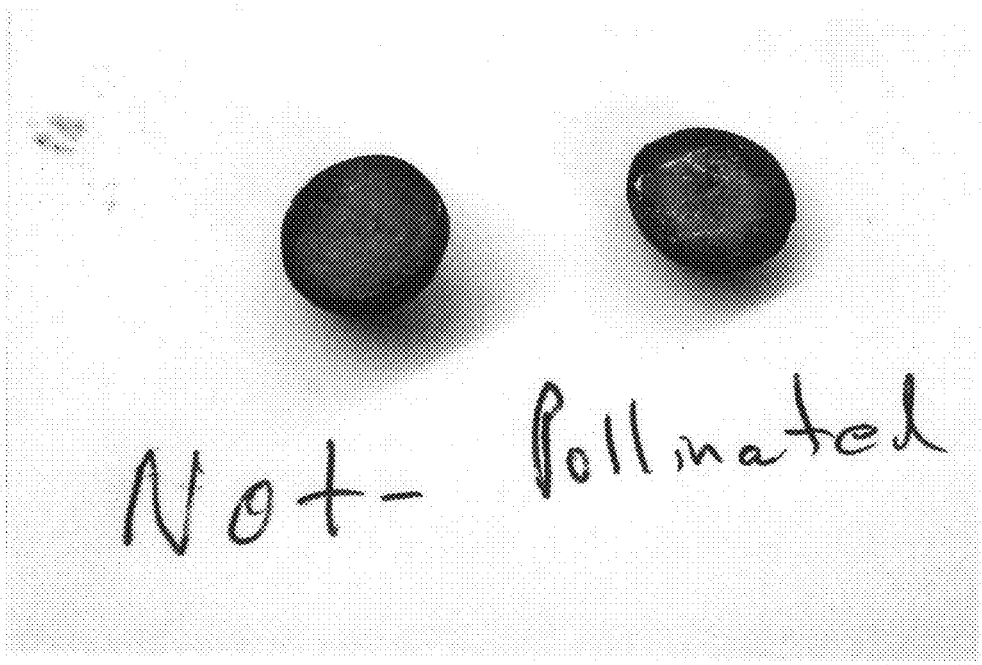
FIG. 5 Is a photographic illustration of slices or fruit of 'A132-926' without seeds (not pollinated).
Figure 6:
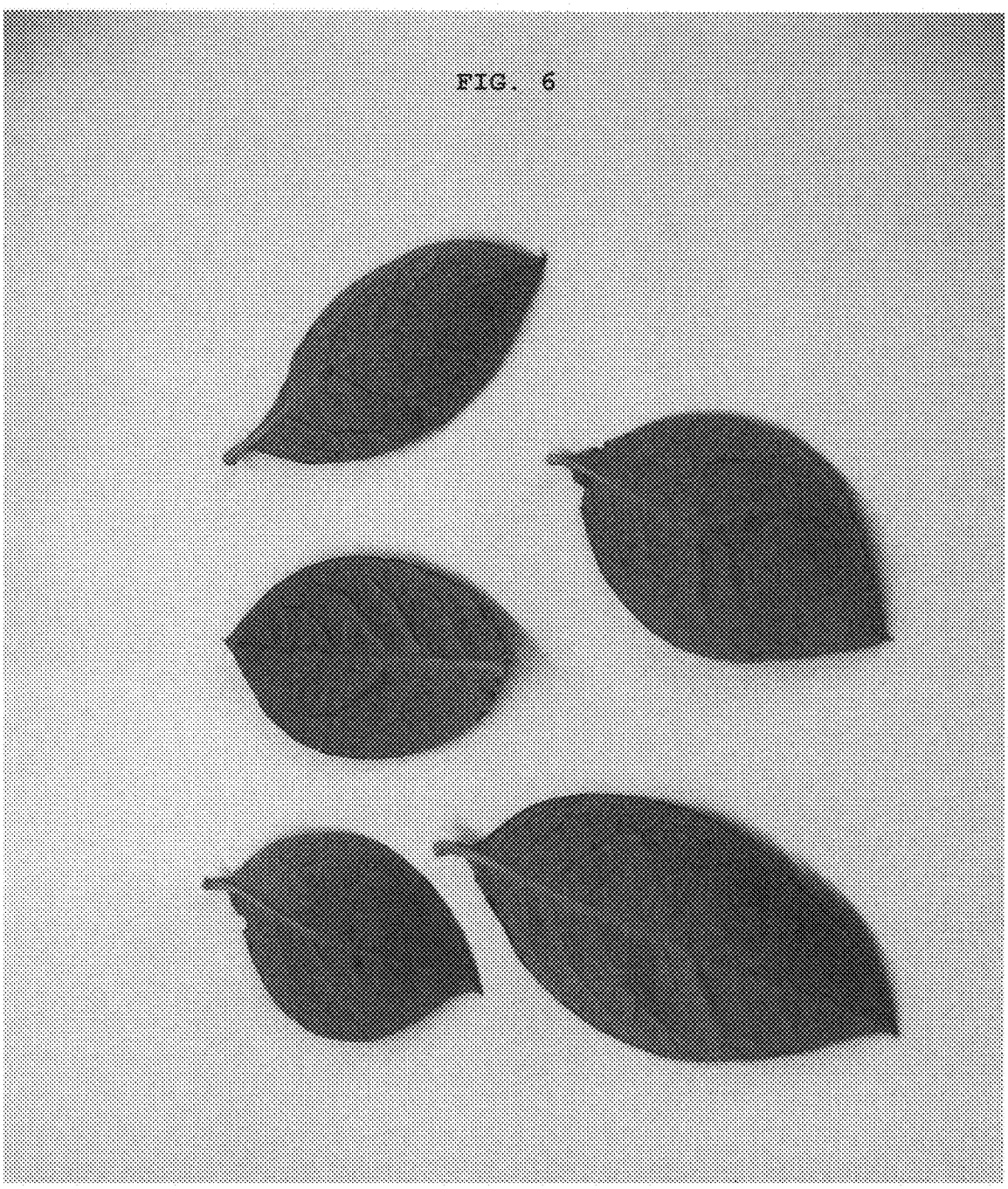
FIG. 6 Is a photographic illustration of the leaves and leaf stems of the plant 'A132-926'.
Figure 7:
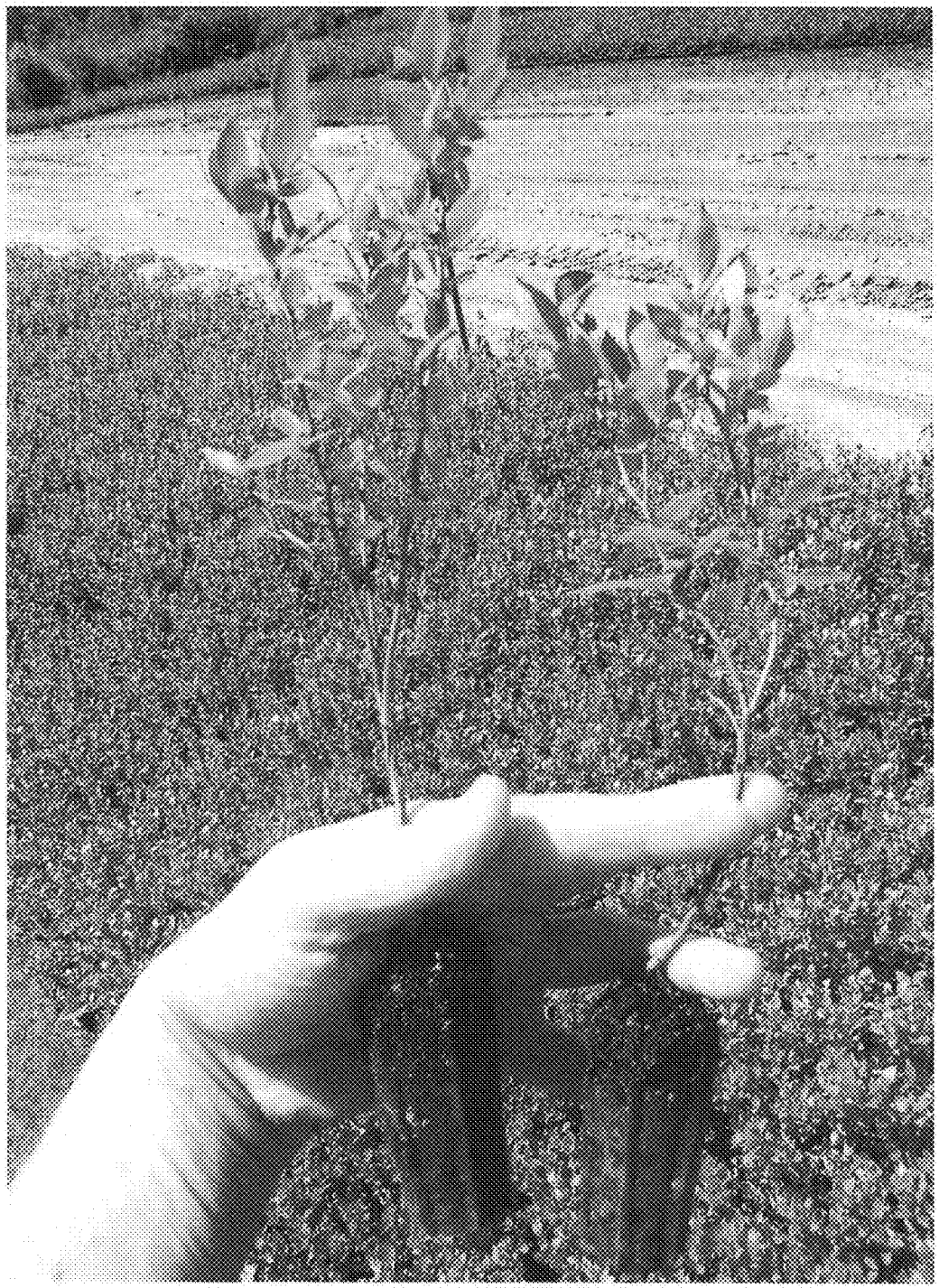
FIG. 7 Is a photographic illustration of the spacing of a stem of 'A132-926'.

Color descriptions, except those given in common terms, use designations cited from The Royal Horticulturel Society (R.H.S.) Colour Chart. Original publication date 1966, second publication date 1995. Colors in the drawings are only approximate, in cases where the colors in the drawings differ from the RHS color designation given herein, the RHS designation should be considered the more accurate.

DETAILED DESCRIPTION OF THE VARIETY

The following is a detailed botanical description of the new and distinct variety of blueberry, its flower, fruit, foliage and stems, based on observation of specimens grown at Grand Junction, Mich.

The following measurements were from a plant 5 years of age grown in a 16 gallon container in Grand Junction, Mich.

Height of plants: 4 to 5 feet.

Trunk: Crown width narrow 15 to 18 inches diameter.

Suckering tendency: Medium.

Leaves:

*Leaf arrangement*.—Alternate, deciduous, non-serrated, smooth edges.

*Leaf length*.—Length 5.0 cm.

*Leaf width*.—3.0 cm.

*Leaf outer edge*.—Smooth.

*Leaf shape*.—Ovate.

*Leaf nodes are* 1.0 *to* 1.5 mm *in length Leaf petiole length*.—2.0 mm (very short).

*Mature leaf color*.—Is RHS 147-A. New leaf color is RH5 N144-B.

*New fruiting lateral stem color*.—143C.

*Summer color of bottom surface of leaves*.—138-A.

*Autumn color of leaves*.—Orange (RHS 175 A).

Flowers: Flowers appear when foliage has 35% emergence.

Petals:

*Pollen color*.—RHS 10D.

*Pollen production per flower*.—1.1 mg/flower/day to 2.2 mg.

*Flower type*.—Flower bracts are deciduous and glaucous. They appear when the foliage has 35% emergence. Flowers are borne on racemes that are longer than pedicles.

*Flower corolla shape and size*.—Slightly to moderately urceolate, 10.24+−1.75 cm.

*Corolla color*.—RHS N155-A.

*Color of the fresh anthers in flower at antheseis*.—RHS 20A.

*Diameter of corolla tube at widest point*.—9.3 1.3 cm.

*Color of corolla tube*.—RHS N155-A.

*Corolla shape and size*.—Slightly to moderately urceolate 10.24+−1.70 cm.

*Corolla color at anthesis*.—(RHS 157D).

*Pedicel and peduncle color*.—(RHS 144C).

*Calyx color at anthesis*.—CRAS 144D.

*Number of calyx lobes*.—5.

*Calyx surface*.—Prodruding slightly 3.0 mm to 3.3 mm.

*Flowering period*.—Appears when the foliage has 35% emergence in greenhouse at Grand Junction, Mich.

*Flower cluster*.—Medium.

*Number of flowers per cluster*.—6 to 9.

*Berry cluster*.—Loose and open.

*Pedicel length at unripe green fruit*.—0.5 to 1.0 mm, mostly 0.9.

*Pedicel color*.—(RHS 46-A).

*Peduncle length at berry maturity*.—1.5+−0.3 cm.

*Number of berries per cluster*.—Normally 7.

*Berry shape*.—Very round only partially flattened.

*Berry weight*.—2.78-0.49 grams.

*Berry width*.—1.8+−1 mm.

*Berry skin color* (*ripe on plant*).—98-C-RHS.

*Berry skin color after bloom rubbed off*.—N186-A-RHS.

*Berry acidity*.—Low.

*Berry quality*.—Very firm with small picking scar.

*Berry sweetness*.—High.

*Seed size*.—Length 1.42+−0.18 mm. Average weight 0.5 mg.

*Color of mature seeds*.—167A RH5.

*Internal flesh color*.—148-D, RH5.

*Berry firmness*.—9.0 rated on 1-10 scale, 10 being best.

*Berry flavor*.—5 — scale of 1-5, 5 is best.

*Berry texture*.—Solid flesh, fresh in flavor.

*Maturity date of berry*.—50% ripeness occurs 10 days prior to Star and 13 days prior to Misty in Earleton, Fla. on April 21$^{st}$. First commercial harvest (50% of the fruit ripe) typically April 21$^{st}$ at Earleton, Fla. Last commercial harvest typically May 6.

*Productivity*.—Yields up to 15 pounds of berry per plant per year at maturity.

Plant stems are cold hardy to minus 10 degrees F. (minus 23 degrees C.).

*Plant stem color*.—One and 2 year stems are colored green (RHS 143C).

*Fruiting stem color*.—Mostly green with some reddish (RHS 46A).

*Fruit stem length*.—1.0, 0.9, 0.7, 0.5.

*Intensity of bloom of fruit*.—Medium.

*Color of branches*.—3 or more years — Brown (RHS 177B).

The berries are very suitable for fresh marketing and can be stored for 21 days at temperatures 33 to 40 degrees F. (0.5 to 4.4 degrees C.).

The following ratings are on a scale of 1-5, 5 is best.

*a. Spreading habit*.—4.0.

*b. Upright*.—4.0.

*c. Leaf to fruit ratio*.—5.0.

*d. Time of flower*.—Early mid 5 is best for the climate where this cultivar is recommended.

*e. Harvest*.—Early 5 is best for the climate where this cultivar is recommended.

*f. Fruit size*.—1.8 cm wide; 1.3 cm height+−1.0 mm.

*g. Fruit color*.—89C RHS.

*h. Fruit firmness*.—4.5.

*i. Stem scar*.—5.0.

*j. Tightness of cluster*.—4.5.

*k. Foliar diseases*.—5.0.

*l. Fruit rots.*—4.0.
*m. Yield.*—5.0.
*n. Moderate pruning.*—4.0.
*o. Plant vigor.*—5.0.

Resistance to diseases, insects, and mites:
*Phytophthera.—Phytophthera cinnamoni.*
*Stem blight.—Botrytis dothidea.*
*Leaf spot.—Glomerella cingulata.*

GENERAL COMPARISON WITH SIMILAR VARIETIES

'A132-926' is most similar to Sharpblue, Misty and 'Star' (patented). A comparison of 'A132-926' with these three varieties is as shown below.

A. 'A132-926' characteristics:
1. *Spreading upright growth.*—4 to 5 feet tall.
2. *Fruit quality.*—4.0.
3. *Fruit size.*—4.0.
4. *Ripening time.*—4.0.
5. *Yield.*—5.0.
6. *Prune moderate yearly.*—4.0.

B. Misty characteristics:
1. *Upright growth habit.*—4 to 5 feet tall, 2.5 to 3 feet wide.
2. *Fruit quality.*—3.0.
3. *Fruit size.*—3.0.
4. *Ripening time.*—3.0.
5. *Yield.*—4.0.
6. *Prune moderately yearly.*—4.0.

C. Sharpblue characteristics:
1. *Spreading outward growth.*—Slightly upright 3.5 to 4.5 feet.
2. *Fruit quality.*—2.0.
3. *Fruit size.*—3.0.
4. *Ripening time.*—3.5.
5. *Yield.*—3.0.
6. *Prune moderately yearly.*—4.0.

D. Star characteristics:
1. *Spreading outward slightly, upright growth.*—4 to 5 feet.
2. *Fruit quality.*—5.0.
3. *Fruit size.*—4.0.
4. *Ripening time.*—4.0.
5. *Yield.*—4.0.
6. *Prune moderately yearly.*—4.0.

LEAF COMPARISON WITH SIMILAR VARIETIES

'A132-926':
*Leaf arrangement.*—Alternate, deciduous, non-serrated, smooth edges.
*Leaf length.*—5.0 cm.
*Leaf width.*—3.0 cm.
*Leaf petiole length short.*—2.0 mm.
*Leaf edges.*—Smooth outer edge.
*Leaf shape.*—Ovate.
*Top leaf color dust off.*—147-A.
*Top leaf color dust on.*—139-A.
*Bottom leaf color.*—138-A.
*New fruiting lateral stem color.*—143-C.
*Calyx.*—Crown protruding.
*Leaf nodes on fruiting laterals close.*—1.0, 1.5, 1.8, 1.3, 2.0 cm.
*Fruit stems color.*—46-A.
*Fruit stem length.*—1.0, 0.9, 0.7, 0.5.

Misty:
*Leaf arrangement.*—Alternate, deciduous.
*Leaf length.*—5.6 cm.
*Leaf width.*—2.7 cm.
*Leaf edges.*—Non-serrated smooth edges.
*Leaf shape.*—Ovate.
*Leaf nodes on fruiting laterals.*—1.6, 1.9, 2.0, 2.4 cm.
*Fruit stem length.*—1.0, 0.9, 0.8, 0.7 cm.

Star characteristics:
*Leaf arrangement.*—Alternate, deciduous.
*Leaf length.*—7.5 cm.
*Leaf width.*—3.2 cm.
*Leaf edges.*—Non-serrated, smooth.
*Leaf nodes on fruiting laterals.*—2.9, 2.8, 2.6, 2.0 cm.
*Fruit stem length.*—0.9, 1.1, 1.0, 0.8 cm.

Sharpblue characteristics:
*Leaf arrangement.*—Alternate, deciduous.
*Leaf length.*—3.5 to 5.0 cm.
*Leaf width.*—2.6 to 3.2 cm.
*Leaf edges.*—Non-serrated, smooth edges.
*Leaf shape.*—Ovate.
*Fruit stem length.*—0.8, 1.1 1.4 cm.
*Leaf nodes on fruiting laterals.*—1.0, 0.8, 0.7 cm.

What is claimed is:

1. A new and distinct variety of blueberry plant, substantially as illustrated and described herein.

* * * * *

Not - Pollinated